United States Patent [19]
Delagnes et al.

[11] Patent Number: 6,040,853
[45] Date of Patent: Mar. 21, 2000

[54] PROCESS FOR DETECTING SURFACE DEFECTS ON A TEXTURED SURFACE

[75] Inventors: Philippe Delagnes, Baye; Dominique Barba, Carquefou, both of France

[73] Assignees: Laboratoire Central des Ponts et Chaussees, Paris; L'Institut de Recherche et D'Enseignement Superieur aux Techniques de Electronique, Nantes Cedex, both of France

[21] Appl. No.: 08/957,987

[22] Filed: Oct. 2, 1997

[30] Foreign Application Priority Data

Oct. 2, 1996 [FR] France .................................. 96 11997

[51] Int. Cl.⁷ .............................. H04N 7/18; G06K 9/00
[52] U.S. Cl. ..................... 348/128; 348/148; 348/150; 382/110; 382/152; 382/205; 356/445; 73/104
[58] Field of Search ..................... 348/125, 127, 348/128, 132, 134, 88, 148, 150, 92; 382/149, 1, 152, 205, 141, 110, 8; 356/445, 237; 73/104, 105, 146; H04N 7/18; G06K 9/00

[56] References Cited

U.S. PATENT DOCUMENTS

| | | | |
|---|---|---|---|
| 4,253,113 | 2/1981 | Decavel et al. ........................ | 348/132 |
| 4,546,384 | 10/1985 | Kowalski ................................ | 382/152 |
| 4,573,190 | 2/1986 | Tsumoda et al. ......................... | 382/1 |
| 4,653,316 | 3/1987 | Fukahara ................................. | 73/146 |
| 4,879,752 | 11/1989 | Annue et al. ............................. | 382/1 |
| 4,922,337 | 5/1990 | Hunt et al. ............................. | 348/88 |
| 4,958,306 | 9/1990 | Powell et al. .......................... | 702/40 |
| 5,245,424 | 9/1993 | Yoshida ................................. | 358/106 |
| 5,255,329 | 10/1993 | Tanimizu et al. ........................ | 382/8 |
| 5,544,256 | 8/1996 | Brecher et al. ......................... | 382/149 |
| 5,774,177 | 6/1998 | Lane ...................................... | 348/88 |
| 5,845,002 | 12/1998 | Heck et al. ............................ | 382/110 |
| 5,850,468 | 12/1998 | Yokoyama et al. ..................... | 382/149 |

FOREIGN PATENT DOCUMENTS 2402868   9/1977   France .

*Primary Examiner*—Howard Britton
*Assistant Examiner*—Tung Vo
*Attorney, Agent, or Firm*—Wolf, Greenfield & Sacks, P.C.

[57] ABSTRACT

A process for detecting defects in a textured suface, particularly on a highway. The process consists in displacing with respect to the surface a camera presenting an inclination and in processing by processing systems the successive images taken by the camera. A mathematical processing is effected on sub-images, corresponding to the same spatial portion of the surface, taken at different consecutive instants.

9 Claims, 2 Drawing Sheets

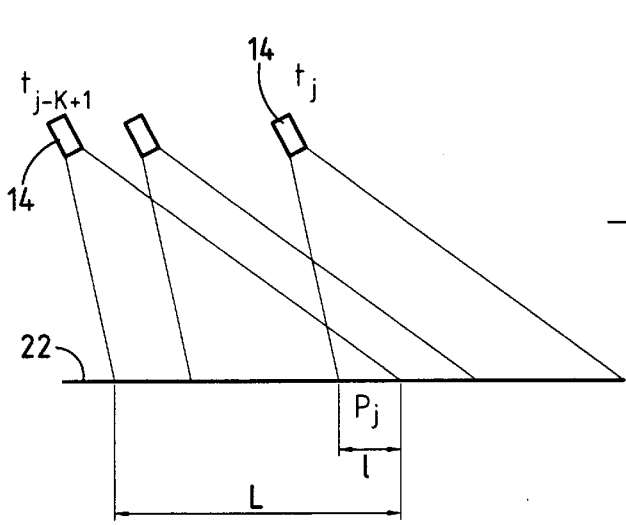
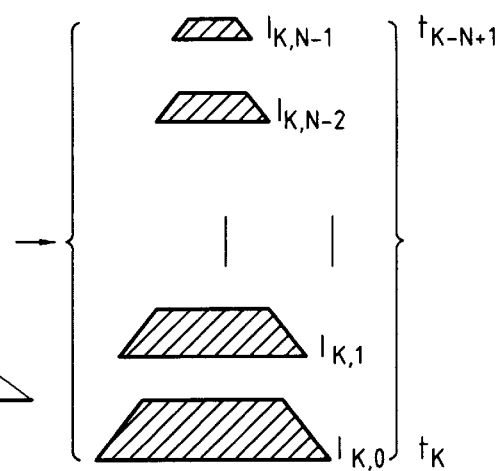
FIG.3  FIG.4
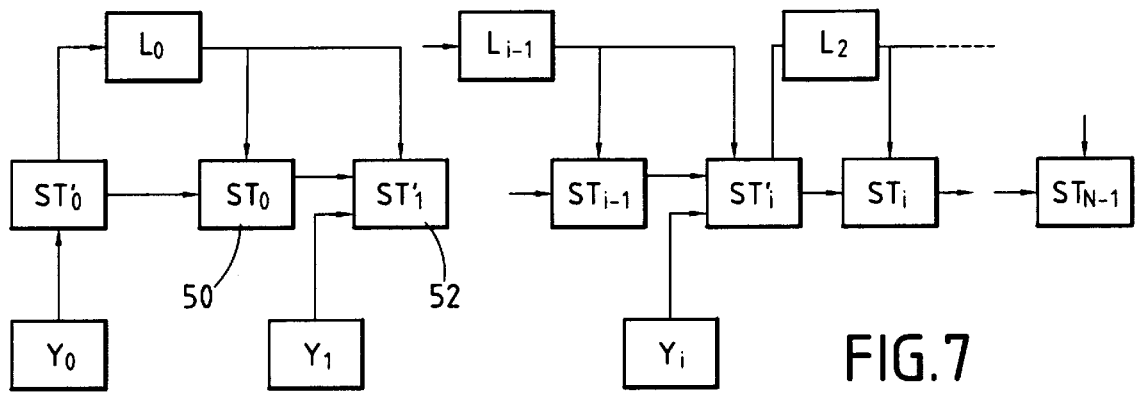
FIG.7
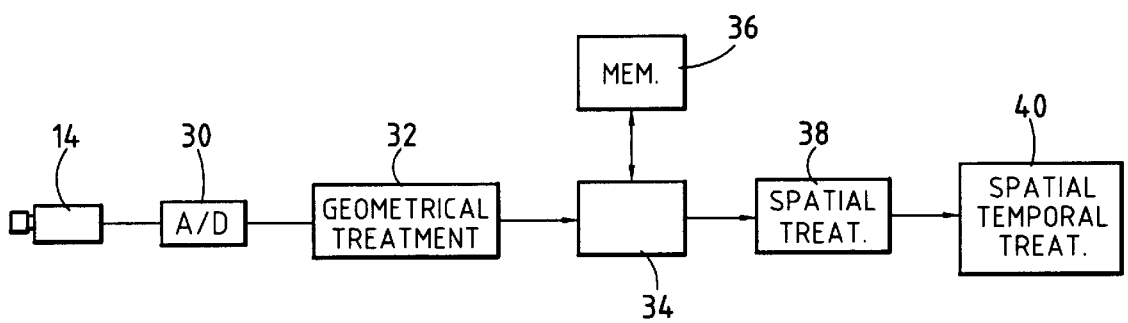
FIG.6

PROCESS FOR DETECTING SURFACE DEFECTS ON A TEXTURED SURFACE

FIELD OF THE INVENTION

The present invention relates to a process for detecting surface defects in a substantially plane textured surface. In the case of a substantially plane textured surface, the detection of defects raises particular problems, due to the interference, at the optical level, between the texture of the surface and the defects that said surface may present. This is particularly but not exclusively the case of the detection of defects on a highway.

BACKGROUND OF THE INVENTION

When it is desired to check the quality of a highway surfacing, the state of a section of highway can be inspected directly by the human eye. Such an inspection furnishes a very detailed analysis of the degradations of the surfacing. However, it will be understood that such a technique is extremely long and therefore extremely expensive to carry out. It is for this reason that it has been sought to develop techniques for automatically detecting such defects.

Among these known techniques may be mentioned the one consisting in placing on a vehicle a bar of CCD detectors whose axis of sight is perpendicular to the plane of the road. In this technique, the images taken by the optical sensor constitute a pavement of the highway. They are exploited to deduce therefrom the presence of a possible defect. However, such processes are relatively imprecise by reason, on the one hand, of the texture of the highway and, on the other hand, of the sensitivity to the conditions of illumination. In addition, they are relatively slow, particularly by reason of the acquisition and processing of high-definition images which correspond to large volumes of data.

Up to now, the problem of degradation of the highway surfacing has been considered However, it will be readily understood that a similar problem is encountered as soon as the surface on which it is desired to detect surface defects has a certain texture presenting a random optical appearance. This will be the case for example of the detection of defects in a fabric, or more precisely in a web of fabric or the case of the detection of possible defects in a surfacing web for example made of laminated material.

Another problem to be solved, in the case of exploiting an image for detecting a defect in a textured surface is that, if it is desired to analyze images corresponding to relatively large surfaces and if the defects are of relatively small dimensions, the problem of the definition of the optical sensor serving to make the shot is raised, in particular when the dimension of the defects may become of the order of a pixel or even smaller than a pixel. In that case, the detection of a defect will become very difficult or highly random, particularly due to the analog-digital conversion that it is necessary to effect to process the image obtained.

It is an object of the present invention to provide a process for detecting surface defects which allows a detection over a relatively large surface and with a relatively high speed of detection while ensuring a good quality of detection of the possible defects of this textured surface.

SUMMARY OF THE INVENTION

To that end, in accordance with the invention, the process is characterized by the following steps of:

a) making, with the aid of an optical sensor presenting an inclination of sight with respect to the substantially plane textured surface and being in relative movement with respect to this surface, a succession of images of parts of this surface at successive instants, each image corresponding to a surface part of length L in the direction of displacement, each image being offset from the preceding one by a length 1, 1 being equal to L/K with K, a whole, greater than 2;

b) defining sub-images corresponding to elementary portions of the surface whose length is equal to 1 in the direction of displacement, whereby for the length of portion of surface 1, K sub-images of this portion are therefore available;

c) extracting from these K consecutive sub-images N sub-images (Ii) corresponding to the same portion of the surface of length 1 at N successive instants with N included between 2 and K;

d) applying to each of the N sub-images (Ii) the same spatial mathematical processing in order possibly to demonstrate a configuration of presumed defect, which gives a processed intermediate sub-image (Yi);

e) applying to the first processed elementary sub-image (Yo) a combinatorial algorithm for detection of presumed defect in the elementary sub-image, whereby a spatial and temporal sub-image $ST_0$ is obtained;

f) iteratively repeating the application of said combinatorial algorithm to the spatial and temporal sub-image $ST_{i-1}$ obtained at instant ti−1 and to the processed elementary sub-image Yi in order to obtain a spatial and temporal sub-image $ST_i$ up to i=N−1; and g) obtaining with the spatial and temporal sub-image $ST_{N-1}$ the image of the elementary portion of the textured surface with its possible defects.

It will be understood that, thanks to the invention, the determination of a defect in an elementary portion of the textured surface results from the processing of sub-images corresponding to an elementary position of the surface occupying "a fixed position", these sub-images being taken at different successive instants. Thanks to the particular processing defined hereinabove, an efficient detection of the presence of possible defects may be obtained, using a camera having a relatively wide field, which makes it possible rapidly to detect the possible defects in relatively large overall surfaces.

According to a first form of embodiment, more particularly applied to the detection of defects in a highway, the optical sensor is constituted by a camera mounted on a vehicle which, of course, moves with respect to the highway.

According to a second form of embodiment, the optical sensor is fixed and the textured surface is moved at a constant speed with respect to the optical sensor. This second embodiment is particularly well adapted to the detection of possible defects in a fabric or in a web of laminated surfacing.

BRIEF DESCRIPTION OF THE DRAWINGS

The invention will be more readily understood on reading the following description with reference to the accompanying drawings, in which:

FIG. 3 illustrates the taking of successive images of parts of surface.

FIG. 4 shows the successive sub-images of the same portion of surface taken at consecutive instants.

FIG. 6 is a very schematic view of the means for processing the data delivered by the optical sensor; and FIG. 7 is a block diagram illustrating the implementation of the combinatorial algorithm for elaborating the spatial and temporal sub-images.

DESCRIPTION OF PREFERRED EMBODIMENTS

As has already been indicated, the process for detecting defects on the textured surface is based on the processing of successive images taken with the aid of an optical sensor presenting an inclination with respect to the surface to be checked, i.e. non-perpendicular thereto, and on the exploitation of the successive images taken. The relative displacement of the optical sensor with respect to the surface to be checked may be obtained either by displacement of the optical sensor with respect to the surface or by displacement of the surface with respect to the optical sensor.

Figure 1:
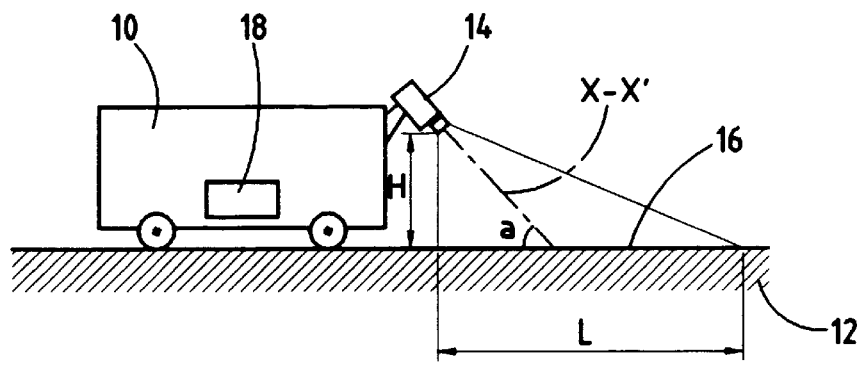
FIG. 1 is a simplified view of the installation used for carrying out the process in the case of detecting defects in a highway.

Referring now to the drawings, FIG. 1 schematically illustrates the device used for detecting defects on a highway. This Figure schematically shows a vehicle 10 moving over the highway 12. A camera 14 or other like optical sensor is mounted on the vehicle so that its optical axis XX' makes with the surface of the highway an angle a different from 90 degrees. Depending on the aperture of the camera 14, each image taken corresponds to a length of portion of highway L. This length L depends, of course, on the height H of the camera and on the aperture thereof. As will be explained hereinafter, the inclination and height are defined so that a good image of the whole portion of highway 16 is obtained despite the different inclinations of the light rays. This Figure also schematically shows the processing systems 18 embarked on the vehicles for processing the signals delivered by the camera 14 in order to detect the presence of possible defects.

Figure 2:
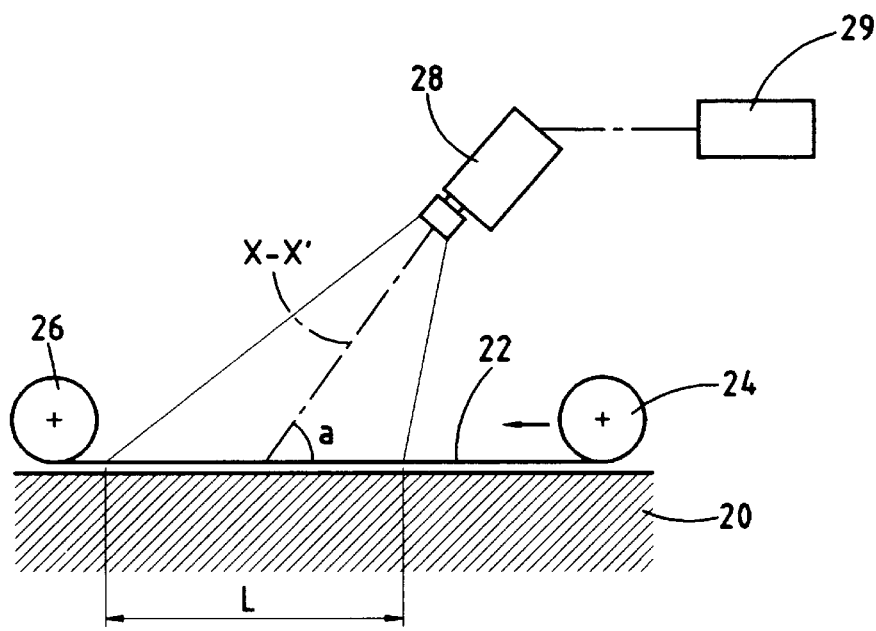
FIG. 2 is a simplified view of the installation in the case of detecting defects on a fabric.

FIG. 2 illustrates the opposite displacement when, for example, it is desired to detect possible defects on a web of fabric which also constitutes a textured plane surface. A supporting plane surface 20, over which the web of fabric 22 moves, is schematically shown, this web being initially stored on a roller 24 and driven by a drive roller 26. A fixed camera 28 whose optical axis XX' makes an inclination a with the portion of web of fabric 22 moving over the support surface 20, takes successive images of the web of fabric. System 29 processes, as will be described hereinbelow.

This form of embodiment is particularly well suited to the detection of defects in a web of material presenting a textured surface and which is easy to move. This is particularly the case not only of a web of fabric, but also of a plank or piece of rough wood or of a metal product of elongated shape.

In the following description, the case of detecting defects on a highway will be considered, corresponding therefore to FIG. 1. However, it goes without saying that this description may be directly transposed to the case of detection in accordance with the form of embodiment of FIG. 2.

The successive images obtained at the different instants are used for forming the sequences of sub-images, each of the sequences being associated with an elementary portion of surface. A first mathematical processing partially or completely corrects the effects due to the perspective as the optical axis of the camera is inclined. These mathematical image processings are known per se and are not explained here. They make it possible to give each sub-image a standard rectangular or trapezoidal shape less accentuated than the initial trapezoidal shape.

As has already been indicated, the detection of possible defects in an elementary portion (P) of the surface S of length 1=L/K is based on the processing of a sequence of sub-images corresponding to this portion (P) of surface obtained from images observed at successive instants and offset in space by the length 1.

FIG. 3 illustrates the construction of the sequence of sub-images ($I_{j,i}$) from the successive images allowing the observation of ($P_j$). This Figure shows in particular the successive positions of the camera 14 for which the images are taken. An elementary portion of the surface of index j (noted ($P_j$)) is observed in the sequence of images going from instant $t_{j-K+1}$ to instant $t_j$. The sub-image corresponding to $P_j$ is extracted from each of them.

The sequence of sub-images ($I_{j,i}$) corresponding to the observation of an elementary portion ($P_j$) of the surface forms the spatial and temporal signal which serves as input for the analysis step with a view to detecting possible defects on ($P_j$). FIG. 4 shows the sub-images ($I_{j,i}$) before processing thereof.

As will be explained in greater detail hereinafter, by iteratively repeating the mathematical processing for detection of possible defects on each of the successive elementary portions ($P_j$) constituting the complete surface to be analyzed, the defects possibly present are thus detected in the overall surface.

Figure 5:
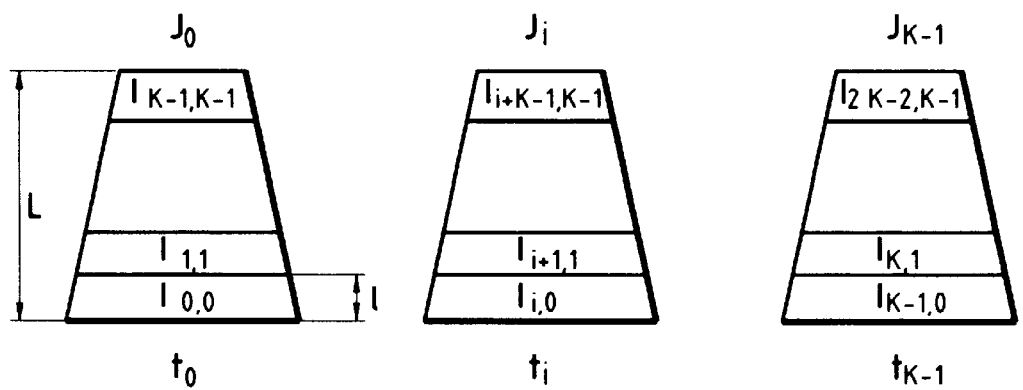
FIG. 5 illustrates the obtaining of the sub-images at different consecutive instants in the image of a part of surface.

FIG. 5 illustrates in greater detail the "cutting" of each image into sub-images $I_{j,i}$. The image $J_i$ taken at instant $t_i$ is cut into K sub-images $I_{i+k,k}$, k varying from 0 to K−1, so that each sub-image corresponds to a portion of highway surface of the same length 1=L/K. At instant $t_0$, the image taken shows sub-images $I_{0,0}$ to $I_{K-1,K-1}$. At instant $t_i$, the image shows images $I_{i,0}$ to $I_{i+K-1,K-1}$.

Reciprocally, if the portion of surface $P_j$ is considered, it is present in the image taken at instant j in $I_{j,0}$ corresponding to the "lower edge of image $J_j$", in the image taken at instant j−1 in $I_{j,1}$, . . . , in the image taken at instant K−1 in $I_{j,K-1}$ corresponding to the "upper edge of the image $J_{j-K+1}$". K sub-images $I_{j,k}$ are thus obtained, k varying from 0 to K−1 of the same elementary portion ($P_j$) of length 1 of the highway at K different successive instants $t_{j-K+1}$ to $t_j$.

In the following, the index of the portion of highway will be set aside, the conventions adopted for the indices making it possible to refer to the sub-images Ii, i varying from 0 to K−1 to designate the K sub-images corresponding to a portion (P) of highway.

In accordance with the principle of the invention, detection of the defects is effected by processing N sub-images corresponding to the same elementary spatial portion of highway, these sub-images being taken at N different consecutive instants. It will be readily understood that N must be at least equal to 2 and that N is at the most equal to K. In a particular form of embodiment, N=K=11. N and K are preferably included between 6 and 15.

It will now be described how the N spatial sub-images corresponding to the same elementary portion of highway are mathematically processed at N different instants.

Processing, in the form of a simple temporal addition, might be effected directly at the level of the pixel of the sub-images obtained and converted into digital form. However, the inventors have demonstrated that such processing proved unsatisfactory to demonstrate the possible presence of defects clearly.

Consequently, according to the invention, instead of applying a processing directly at the level of the pixels constituting the different sub-images, a prior processing is effected, making it possible to work on configurations or more exactly groups of pixels capable of corresponding, in a sub-image, to a surface defect. A process known per se for effecting this preliminary processing step consists in employing an analysis grid which is therefore the same as leaving the pixel level to manipulate primitives whose nature corresponds better to the problem to be treated. Use of this analysis grid per line may consist in employing a markovian model which is well known per se. The subsequent processing of the sub-images which will be described is therefore applied to the sub-images modified by application of the markovian model. Other processings may be used, as will be explained hereinafter.

FIG. 6 illustrates the whole process of detection in simplified manner. The analog signals delivered by the camera 14 are converted into digital signals by the converter 30. The latter is connected to a digital image processing system 32 which employs the process of correction of the images and of "cutting" the images into sub-images. System 34 brings into register the digital sub-images corresponding to the same elementary portion of surface and memorizes them in 36. System 38 effects spatial processing of each sub-image for example by application of a markovian model. Finally, system 40 effects the spatial and temporal processing of the sub-images 42 which will be described hereinafter with reference to FIG. 7. This latter system makes it possible to obtain the image of each elementary portion of surface with its possible defects.

Referring now to FIG. 7, the processing of the different sub-images obtained by the method described previously will now be described in greater detail. This Figure explains the spatial and temporal processing system 40 of FIG. 6. In FIG. 7, the reference $Y_i$ designates the spatial sub-image obtained at instant $t_i$ and to which the extraction grid has been applied. References $L_i$ indicate the steps of markovian segmentation applied to the spatial-temporal images. References $ST'_i$ designate initial spatial-temporal sub-images and $ST_i$, processed spatial-temporal sub-images. The first spatial-temporal image ST is in fact identical to the spatial image $Y_0$. By markovian segmentation $L_0$ the spatial-temporal sub-image $ST_0$ is obtained. In the following step referenced 50, the second spatial sub-image $Y_1$ is combined with the first spatial-temporal image $ST_0$ with the aid of a combinatorial algorithm which will be defined hereinafter. By markovian segmentation, the spatial-temporal image of row 1 is obtained at step 52.

More generally, it will be understood that, in order to obtain the spatial-temporal sub-image of row i, one starts from the spatial-temporal sub-image of row i−1 which is combined with the spatial observation of row i, this giving the initial spatial-temporal sub-image then, by markovian segmentation, the definitive spatial-temporal image of row i is obtained. It will be understood that this operation of application of the combinatorial algorithm is carried out repeatedly up to i=N−1. The spatial-temporal image of row N−1 to which the markovian segmentation has been applied, furnishes a sub-image on which the defect clearly appears, if such a defect is effectively present in the elementary portion of surface in question.

A preferred form of embodiment of the combinatorial algorithm will now be described in greater detail, which makes it possible to obtain, from the spatial sub-image Yi and the spatial-temporal sub-image $ST_{i-1}$, the spatial-temporal sub-image $ST_i$.

The spatial sites of $Y_i$ are all carried over in $ST'_i$.

The sites of $ST_{i-1}$ having for descriptor 1 in $L_{i-1}$ are projected in $ST'_i$. For any site s projected from $ST'_i$ in accordance with the following conditions:

if there is located near s a site s' coming from $Y_i$ and such that the centres of s and s' are 8-adjacent, the two sites are transformed into a single resultant site $s_{resultant}$. Two cases are distinguished:

s and s' are not perpendicular with respect to each other: a fusion of the two sites is made, and the characteristics of the resultant site are as follows:

position: the position of $s_{resultant}$ is that of s': $(x_{resultant}, y_{resultant})=(x_{s'},y_{s'})$ orientation: the orientation $\theta_{resultant}$ is that of the site s or s' which attains $\max(st_{i-1}(s),y_i(s'))$ if (si $st_{i-1}(s)=y_i(s')$, $\theta_{resultant}=\theta_s$, amplitude: $st'_i(s_{resultant})=\max(st_{i-1}(s),y_i(s'))+1/\eta.\min(st_{i-1}(s),y_i(s'))$.

s and s' are perpendicular with respect to each other: s is eliminated, hence $s_{resultant}=s'$.

if there is no site s' coming from $Y_i$ and such that the centres of s and s' are 8-adjacent, then s is conserved as such: $s_{resultant}=s$.

The markovian segmentation $L_i$ obtained from $ST'_i$ furnishes important indications by distinguishing in $ST'_i$ the sites which may be considered as significant from those which are not. The field of the descriptors $L_i$ is therefore used for re-assessing the amplitude of the sites of $ST'_i$, which leads to the final spatial-temporal observation $ST_i$:

For any site s of $ST'_i$:

if s comes from $Y_i$ (spatial origin), its amplitude remains unchanged: $st_i(s)=st'_i(s)$.

if s comes from $ST_{i-1}$ (temporal origin), the segmentation $L_i$ intervenes.

if $1_i(s)='1'$, the amplitude of s is maintained: $st_i(s)=st'_i(s)$.

if $1_i(s)="0"$, the amplitude of s is reduced: $st_i(s)=1/\eta.st'_i(s)$.

It will be understood that the temporal evolution of st is thus obtained during increase or decrease of the amplitude of these sites. The increase of the amplitude of the significant sites comes from the calculation of $st'_i(s_{resultant})$, during the phase of fusion of two sites not perpendicular to each other. The formula adopted represents a simple manner of calculating the amplitude of the new site (conservation of the maximum amplitude and addition of a fraction of the minimum amplitude), but other modes of calculation of $st'_i(s_{resultant})$ from $ST_{i-1}(s)$ and $y_i$ may be imagined. Decrease of the amplitude of the non-significant sites is obtained during calculation of $ST_i$, in the case of s not being conserved in the over-segmentation ($1_i(s)='0'$).

In the foregoing description, instead of using the sub-images at the level of the pixel to elaborate the spatial-temporal sub-images, a technique of markovian segmentation has been carried out. However, it goes without saying that this process does not limit the invention.

Another process consists in carrying out a process of extraction of related components, known per se, which makes it possible to apply the algorithm to configurations of larger dimensions which improves the detection of the possible defects.

In the case of carrying out the process of extraction of related components, the combinatorial algorithm is applied similarly to what has been described in connection with FIG. 7.

It will be understood that, whatever the variant of the process, the latter consists in processing N sub-images corresponding to the same elementary portion of surface to be checked, the sub-images having been taken at N consecutive instants.

The experiments carried out show that the repeated process applied to these N sub-images makes it possible to obtain a good quality of detection of the possible defects in the elementary portion of textured surface in question.

In particular, it is observed that this repeated processing directed on N sub-images makes it possible to be free from the unknown factors of analog-digital conversion when the possible defects to be detected have a size comparable to the size of the zone covered by a pixel in the image taken.

What is claimed is:

1. Process for detecting surface defects in a substantially plane textured surface, wherein it comprises the following steps of:
   a) making, with the aid of an optical sensor presenting an inclination of sight with respect to the substantially plane textured surface and being in relative movement with respect to this surface, a succession of images of parts of this surface at successive instants, each image corresponding to a surface part of length L in the direction of displacement, each image being offset from the preceding one by a length 1, 1 being equal to L/K with K, a whole, greater than 2;
   b) defining sub-images corresponding to elementary portions of the surface whose length is equal to 1 in the direction of displacement, whereby for the length of portion of surface 1, K sub-images of this portion are available;
   c) extracting from these K consecutive sub-images N sub-images (Ii) corresponding to the same portion of the surface of length 1 at N successive instants with N included between 2 and K;
   d) applying to each of the N sub-images (Ii) the same spatial mathematical processing in order possibly to demonstrate a configuration of presumed defect, which gives a processed intermediate sub-image (Yi);
   e) applying to the first processed elementary sub-image (Yo) a combinatorial algorithm for detection of presumed defect in the elementary sub-image, whereby a spatial and temporal sub-image $ST_0$ is obtained;
   f) iteratively repeating the application of said combinatorial algorithm to the spatial and temporal sub-image $ST_{i-1}$ obtained at instant ti−1 and to the processed elementary sub-image Yi in order to obtain a spatial and temporal sub-image $ST_i$ up to i=N−1; and
   g) obtaining with the spatial and temporal sub-image $ST_{N-1}$ the image of the elementary portion of the textured surface with its possible defects.

2. The process of claim 1, wherein, before step a), there is applied to each sub-image a processing for at least partial correction of the effects of perspective due to the inclination of the optical sensor with respect to the textured surface.

3. The process of claim 2, wherein said spatial mathematical process of step d) consists in applying to said elementary image a markovian model with regular or irregular grid.

4. The process of claim 2, wherein said spatial mathematical processing of step d) consists in effecting an extraction of the related components from the pixels of the sub-image.

5. The process of any one of claims 1 to 4, wherein said optical sensor is a camera mounted on a vehicle and the textured surface is the surface of a highway.

6. The process of any one of claims 1 to 4, wherein said optical sensor is fixed and the textured surface moves linearly with respect to the optical sensor.

7. The process of claim 6, wherein the surface is a web of fabric.

8. The process of claim 6, wherein said surface is a piece of rough wood.

9. The process of claim 6, wherein said surface is that of a long metal product.

* * * * *